US008912128B2

(12) United States Patent
Cha et al.

(10) Patent No.: US 8,912,128 B2
(45) Date of Patent: Dec. 16, 2014

(54) CARBOHYDRATE CHIP FOR DETECTION OF PATHOGEN VIBRIO CHOLERAE AND METHOD OF PREPARING THE SAME

(71) Applicant: Postech Academy-Industry Foundation, Pohang-si (KR)

(72) Inventors: Hyung Joon Cha, Pohang-si (KR); Chang Sup Kim, Pohang-si (KR); Jeong Hyun Seo, Pohang-si (KR); Hwahui Shin, Pohang-si (KR)

(73) Assignee: Postech Academy-Industry Foundation, Pohang-Si (KR)

( * ) Notice: Subject to any disclaimer, the term of this patent is extended or adjusted under 35 U.S.C. 154(b) by 0 days.

(21) Appl. No.: 13/740,367

(22) Filed: Jan. 14, 2013

(65) Prior Publication Data
US 2013/0267433 A1    Oct. 10, 2013

(30) Foreign Application Priority Data

Apr. 10, 2012    (KR) ........................ 10-2012-0037303

(51) Int. Cl.
*G01N 33/569* (2006.01)
*C12Q 1/10* (2006.01)
*C40B 30/04* (2006.01)
*C40B 40/12* (2006.01)

(52) U.S. Cl.
CPC ...... *G01N 33/56911* (2013.01); *G01N 2333/28* (2013.01)
USPC ..................... 506/9; 506/19; 435/7.8; 435/34

(58) Field of Classification Search
CPC . G01N 33/569; G01N 33/56911; C12Q 1/10; C40B 30/04; C40B 40/12

USPC .................... 506/9, 19; 435/7.8, 34
See application file for complete search history.

(56) References Cited

FOREIGN PATENT DOCUMENTS

| KR | 10-0804713 | 2/2008 |
|---|---|---|
| KR | 10-2011-0012794 | 2/2011 |

OTHER PUBLICATIONS

Ngundi et al., "Detection of bacterial toxins with monosaccharide arrays," Biosens. Bioelectron. 2006, 21:1195-1201.*
Seo et al., "A functional carbohydrate chip platform for analysis of carbohydrate—protein interaction," Nanotechnology 2010, 21:215101, 8 pages.*
Kulkarni et al., "Glycan-Based High-Affinity Ligands for Toxins and Pathogen Receptors," Med. Res. Rev. 2010, 30:327-393.*
Chang Sup Kim, et al., "Functional Carbohydrate Microarray for Analyzing Cholera Toxin-Glycan Interactions and Detecting Cholera Toxin", in 2012 Annual Winter Symposium of Korean Society for Glycoscience, Changwon National University, Korea, Feb. 9, 2012.

(Continued)

Primary Examiner — Samuel Woolwine
Assistant Examiner — Kaijiang Zhang
(74) Attorney, Agent, or Firm — Lexyoume IP Meister, PLLC

(57) ABSTRACT

The present invention related to a saccharide-based cholera toxin detection sensor for detection of *Vibrio cholerae* and its use. More specifically, the present invention relates to a carbohydrate chip for detection of *Vibrio cholerae*, a method for detecting *Vibrio cholerae* using the same, and a method for preparing the same, where the carbohydrate chip comprises GM1 pentasaccharide, GM2 tetrasaccharide, asialo GM1 tetrasaccharide, GM3 trisaccharide, galactose-β 1,3-N-acetylgalactosamine, lactose, and sialic acid that are immobilized on the surface of a solid substrate.

6 Claims, 12 Drawing Sheets
(9 of 12 Drawing Sheet(s) Filed in Color)

(56) References Cited

OTHER PUBLICATIONS

Usa Sungkanak, et al., "Ultrasensitive detection of *Vibrio cholerae* O1 using microcantilever-based biosensor with dynamic force microscopy", Biosensors and Bioelectronics, vol. 26, pp. 784-789, Jul. 1, 2010.

Katie A. Edwards and John C. March, "GM1—functionalized liposomes in a microtiter plate assay for cholera toxin in *Vibrio cholerae* culture samples", Analytical Biochemistry, vol. 368, pp. 39-48, Apr. 18, 2007.

C. A. Rowe-Taitt, et al., "A Ganglioside-Based Assay for Cholera Toxin Using an Array Biosensor", Analytical Biochemistry, vol. 281, pp. 123-133, May 2000.

Jeong Hyun Seo, Chang Sup Kim, Hea Yeon Lee, Tomoji Kawai, and Hyung Joon Cha, "Interative Configuration through Force Analysis of GM1 Pentasaccharide—*Vibrio cholera* Toxin Interaction", Anal. Chem. 83, 6011-6017 (Jun. 2011).

* cited by examiner

1 µg/ml 750 ng/ml 500 ng/ml 300 ng/ml 200 ng/ml 100 ng/ml 70 ng/ml 10 ng/ml 5 ng/ml $CtxAB_5$ conc.

CARBOHYDRATE CHIP FOR DETECTION OF PATHOGEN VIBRIO CHOLERAE AND METHOD OF PREPARING THE SAME

CROSS REFERENCE TO RELATED APPLICATION

This application claims priority to and the benefit of Korean Patent Application No. 10-2012-0037303 filed on Apr. 10, 2012, which is hereby incorporated by reference for all purposes as if fully set forth herein.

BACKGROUND OF THE INVENTION (a) Field of the Invention

The present invention relates to a saccharide-based detection sensor and its use, which detection sensor is to detect the existence of Vibrio cholerae in a sample by detecting a cholerae toxin as a Vibrio cholerae detection marker. More particularly, the present invention relates to a carbohydrate chip for detection of Vibrio cholerae, a method for detecting Vibrio cholerae using the same, and a method for preparing the same, where GM1 pentasaccharide, GM2 pentasaccharide, asialo GM1 tetrasaccharide, GM3 trisaccharide, galactose-β 1,3-N-acetylgalactosamine, lactose, and sialic acid are immobilized on the surface of a solid substrate.

(b) Description of the Related Art

The present invention is directed to a technique for detecting pathogen Vibrio cholerae that causes cholera, by means of a micro array (chip) which can be used to analyze and detect the interactions of different organic molecules simultaneously from a small quantity of sample.

A representative pathogenic bacterium, Vibrio cholera is a Gram-negative bacterium with a single, polar flagellum and belongs to the gamma subdivision of the Proteobacteria. Vibrio cholerae is a bacterium causing cholera which still remains a pervasive threat in the Earth. Left untreated, cholera can be fatal with high death rate, averaging 40 to 50%. Hence, the detection and diagnosis of the pathogenic bacterium Vibrio cholerae is a field very critical to the welfare of the human beings, and many efforts have been made to establish it.

Vibrio cholerae releases a substance called "cholera toxin" which causes cholera disease (De Haan, L, Hirst, T R, 2004. Mol. Membr. Biol. 21: 77-92). Hence, the cholera toxin is used as a detection marker for Vibrio cholerae in the Vibrio Cholerae detection system.

More specifically, cholera toxin is a protein enterotoxin secreted by pathogen Vibrio cholerae that is the major causative agent of cholera and used as a detection marker of Vibrio cholerae. Cholera toxin consists of one A subunit and five B subunits. The toxin B subunits bind specifically to GM1 gangliosides on the surface of endothelial cells to help uptake of the toxin A subunit into cells. The toxin A subunit possesses enzymatic (ADP ribosyltransferase) activity involved in accumulation of cAMP in the cells (Fukuta, S, Magnani, J L, Twiddy, E M, Holmes, R K, Ginburg, V, 1998. Infect. Immun. 56: 1748-1753).

There have been developed many detection methods for Vibrio cholerae, mostly based on antibodies or DNA. Antibody-based techniques for detecting Vibrio cholerae include enzyme-linked immunoassorbent assay (ELISA), surface plasma resonance (SPR), quartz crystal microbalance (QCM), microcantilever-based immunosensor, electrochemical immunosensor, and so forth. DNA-based techniques for detecting Vibrio cholerae include polymerase chain reaction (PCR), real time PCR (RT-PCR), multiplex PCR, DNA probe hybridization, and so forth. These techniques are characterized by high sensitivity for detection of Vibrio cholerae but problematic in stability as a sensor for detecting Vibrio cholerae due to a decrease in activity caused by denaturation of antibodies and degradation of DNA by DNase. The antibody-based sensors for detection of Vibrio cholerae has a disadvantage that it requires advanced techniques for immobilizing antibodies with orientation.

Accordingly, there have recently been developed saccharide-based sensors for detection of Vibrio cholerae using the fact that cholera toxin secreted by Vibrio cholerae specifically binds to GM1 gangliosides on the surface of endothelial cells. The saccharide-based sensors for detection of Vibrio cholerae are known to have some advantages over the existing antibody- or DNA-based sensors for detection of Vibrio cholerae (Chen, H, Zheng, Y, Jiang, J-H, Wu, H-L, Shen, G-L, Yu, R-Q, 2008. Biosens. Bioelectron. 24: 684-689). Firstly, GM1 pentasaccharide has the higher structural stability than antibodies, so the sensors for detection of Vibrio cholerae using GM1 pentasaccharide are superior in stability to the antibody-based sensors for detection of Vibrio cholerae. Secondly, GM1 gangliosides have strong affinity to cholera toxin. Lastly, the combining process of GM1 gangliosides and cholera toxin occurs very rapidly.

Recent advances in saccharide-based sensors for detecting Vibrio cholerae have been reported. Some of the sensors are based on the GM1 gangliosides and their analogues immobilized on the surface coated with a lipid film such as a membrane and liposome functionally surface-treated with the saccharides, using a variety of analytical tools, such as surface plasmon resonance (Phillips, K S, Han, J H, Martinez, M, Wang, Z Z, Carter, D, Cheng, Q, 2006. Anal. Chem. 78: 596-603), fluorescent quenching (Song, X, Swanson, B I, 1999. Direct, Anal. Chem. 71: 2097-2107), resonant energy transfer (Ma, G Y, Cheng, Q, 2006. Langmuir 22: 6743-6745), and so forth. These methods are, however, disadvantageously inferior in detection sensitivity.

Some methods are based on the liposomes surface-treated with GM1-gangliosides and their analogues, which liposomes are processed to contain fluorescent reagents (Ho, J A, Wu, L C, Huang, M R, Lin, Y J, Baeumner, A J, Durst, R A, 2007. Anal. Chem. 79: 246-250), colorimetric markers (Ahn-Yoon, S, Decory, T R, Baeumner, A J, Durst, R A, 2003. Anal. Chem. 75: 2256-2261), enzyme (Alfonta, L, Singh, A K, Willner, I, 2001. Anal. Chem. 73: 91-102), electroactive species (Viswanathan, S, Wu, L C, Huang, M R, Ho, J A, 2006. Anal. Chem. 78: 1115-1121), etc. These sensors have high sensitivity in relation to the preceding methods, but the liposome-based sensors for detection of Vibrio cholerae take long time in their fabrication due to complicity of steps and feature some problems in regard to low repeatability and poor stability.

Some studies have been made on the analysis of interactions between GM1 gangliosides and cholera toxin using a microarray based on GM1 gangliosides (Fang, Y, Frutos, A G, Lahiri, J, 2003. Langmuir 19: 1500-1505; Ngundi, M M, Taitt, C R, McMurry, S A, Kahne, D, Ligler, F S, 2006. Biosens. Bioelectron. 21: 1195-1201; and Zhang, J, Zhou, X, 2011. Biosens. Bioelectron. 28: 355-361). However, the analysis in the studies uses GM1 gangliosides and their analogues rather than their carbohydrate moiety as a capture probe, and the liposome used to immobilize the gangliosides has some problems, such as change of structure, non-uniform particle size, aggregation and fusion, and chemical instability, resulting in difficulty and poor repeatability of immobilization. Poor repeatability in the immobilization process may be a serious disadvantage to the sensor for detection of *Vibrio cholerae*.

To solve the problems with liposome used to immobilize gangliosides, the present invention has demonstrated that the carbohydrate chips in which the gangliosides-constituting carbohydrates are immobilized on a solid substrate through chemical modification and covalent bonding is applicable to the analysis of interactions between cholera toxin and carbohydrates constituting the gangliosides and the detection of *Vibrio cholerae* using cholera toxin. In addition, the present invention also uses GM2 tetrasaccharide, asialo GM1 tetrasaccharide, GM3 trisaccharide, galactose-β 1,3-N-acetylgalactosamine, lactose, and sialic acid, in combination with GM1 ganglioside mainly used in the conventional saccharide-based sensors for detection of *Vibrio cholerae*, thereby detecting a low concentration of cholera toxin which is a detection marker for *Vibrio cholerae* and even the cholera toxin actually produced by *Vibrio cholerae*.

SUMMARY OF THE INVENTION

It is an object of the present invention to provide a carbohydrate chip for detection of *Vibrio cholerae* that includes GM1 pentasaccharide, GM2 tetrasaccharide, asialo GM1 tetrasaccharide, GM3 trisaccharide, galactose-β 1,3-N-acetylgalactosamine, lactose, and sialic acid as immobilized on the surface of a solid substrate.

It is another object of the present invention to provide a method for detecting *Vibrio cholerae* by using the carbohydrate chip to detect cholera toxin as a detection marker for *Vibrio cholerae*.

It is still another object of the present invention to provide a method for preparing the carbohydrate chip.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 3b is a fluorescence image showing the GM1 pentasaccharide portion in the results of an analysis on the limitation of detection (LOD) for the whole cholera toxin (ctxAB$_5$) on the carbohydrate chip consisting of seven carbohydrates using the fluorescence immunoassay.

FIG. 4b is a line graph analyzing the fluorescence intensity shown in FIG. 4a.

DETAILED DESCRIPTION OF THE INVENTION

Figure 1:
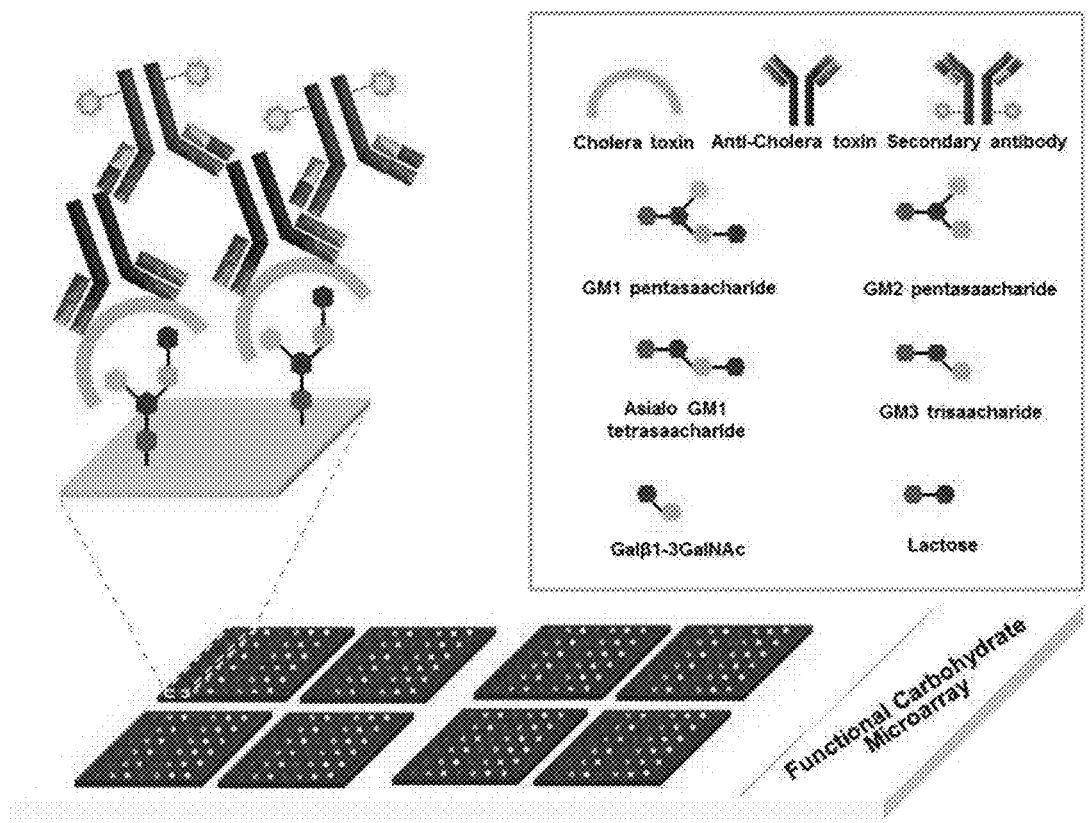
FIG. 1 shows a flat form of a carbohydrate chip consisting of GM1 pentasaccharide, GM2 tetrasaccharide, asialo GM1 tetrasaccharide, GM3 trisaccharide, galactose-β 1,3-N-acetylgalactosamine, lactose, and sialic acid, and a mimetic diagram for detection of cholera toxin.
Figure 2:
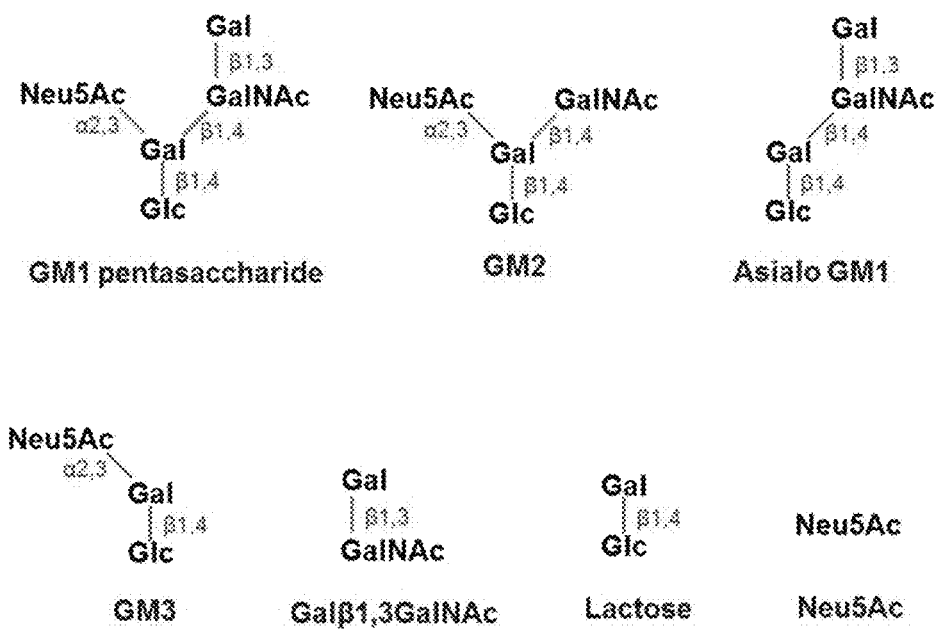
FIG. 2 shows the carbohydrates used in the carbohydrate chip: GM1 pentasaccharide, GM2 tetrasaccharide, asialo GM1 tetrasaccharide, GM3 trisaccharide, galactose-β 1,3-N-acetylgalactosamine, lactose, and sialic acid.

With advantages regarding rapid and simultaneous analysis on a large number of samples, microarray-based techniques have been used as a tool for analyzing interactions of various molecules. In particular, the carbohydrate chip of the present invention has some remarkable advantages over the other analysis tools in analyzing interactions between cholera toxin and GM1 gangliosides and their analogues and detecting cholera toxin as a detection marker for *Vibrio cholerae*. Firstly, it can realize a simultaneous analysis on the interactions between cholera toxin and the carbohydrates using a small amount of sample. Secondly, the carbohydrates immobilized with appropriate spatial and functional orientation can mimic the carbohydrates on the surface of cells and facilitate multivalent interaction that enhances the interactions between cholera toxin and the carbohydrates.

In accordance with one embodiment, the present invention is directed to a carbohydrate chip for detection of *Vibrio cholerae* that includes a solid substrate; and GM1 pentasaccharide, GM2 tetrasaccharide, asialo GM1 tetrasaccharide, GM3 trisaccharide, galactose-β 1,3-N-acetylgalactosamine, lactose, and sialic acid immobilized on the surface of the solid substrate.

The term "carbohydrate chip" as used herein means a microchip having a high density of a carbohydrate, such as of monosaccharides, disaccharides, or polysaccharides, immobilized on the surface of a solid substrate at predetermined intervals. The solid substrate as used herein may be a substrate made of glass, silicon, paper, polymer, or metal, such as iron, steel, aluminum, copper, zinc, tin, lead, nickel, gold, silver, etc. As the present invention uses the fluorescence-based detection method, the solid substrate is preferably a glass substrate.

The term "ganglioside" as used herein refers to a ceramide derivative including several saccharide units and at least one sialic acid and is generally called "GM1", "GM2", or "GM3" depending on the number of saccharide chains and sialic acids.

The term "GM1 pentasaccharide" as used herein refers to a ganglioside (Gal-GalNAc[Neu5Ac]-Gal-Glc) consisting of five saccharides: one N-acetylgalactosamine, one glucose, two galactoses, and one sialic acid, that is, N-acetylneuraminic acid.

The term "GM2 tetrasaccharide" as used herein refers to GM1 pentasaccharide removed of the terminal galactose (GalNAc[Neu5Ac]-Gal-Glc). The term "asialo GM1 tetrasaccharide" as used herein refers to GM1 pentasaccharide removed of the terminal N-acetylneuraminic acid (Gal-Gal-NAc-Gal-Glc). The term "GM3 trisaccharide" as used herein refers to GM1 pentasaccharide removed of the terminal galactose-β 1,3-N-acetylgalactosamine (Neu5Ac-Gal-Glc). The others, "galactose β 1,3-N-acetylgalactosamine (Galβ 1-3GalNAc)", "lactose (Gal-Glc)", and "sialic acid (Neu5Ac)" are disaccharides and monosaccharides constituting GM1 pentasaccharide.

The term "detection of *Vibrio cholerae*" as used herein means determining whether or not the target sample contains *Vibrio cholerae* or whether there is high possibility of finding *Vibrio cholerae* in the sample. For the similar meanings, the term "detection of *Vibrio cholerae*" can be replaced with 'scanning', 'examination', 'determination', or 'analyses. With a view to the purpose of the present invention, the term "detection" as used herein includes the detection sensor determining the presence of *Vibrio cholerae* from the signals generated upon the interaction between the detection sensor and the marker of *Vibrio cholerae*, as well as detection by direct interaction between the detection sensor and *Vibrio cholerae*. Preferably, the present invention uses the fluorescence image analysis to determine the interaction between the cholera toxin used as a detection marker for *Vibrio cholerae* and the detection sensor and thereby to detect the existence of *Vibrio cholerae* in the sample.

Accordingly, the carbohydrate chip of the present invention preferably detects cholera toxin secreted by *Vibrio cholerae* to determine the existence of *Vibrio cholerae* in the sample.

Contrary to the conventional saccharide-based detection sensors for *Vibrio cholera* that use GM1 pentasaccharide only, the carbohydrate chip of the present invention uses GM2 tetrasaccharide, asialo GM1 tetrasaccharide, GM3 trisaccharide, galactose-β 1,3-N-acetylgalactosamine, lactose, and sialic acid, in combination with GM1 pentasaccharide.

Using other saccharides in combination with GM1 pentasaccharide, the carbohydrate chip of the present invention can detect cholera toxin as a detection marker for *Vibrio cholerae* more sensitively and, furthermore, determine the effects of the structures of GM1 pentasaccharide and five monosaccharides constituting GM1 pentasaccharide on the interaction between cholera toxin and GM1 pentasaccharide, thereby contributing to development of a novel inhibitor against the cholera toxin.

Unlike the conventional saccharide-based detection sensors for *Vibrio cholerae* that use liposome or lipid to immobilize gangliosides, the carbohydrate chip of the present invention introduces an amine group (—$NH_2$) into GM1 pentasaccharide, GM2 tetrasaccharide, asialo GM1 tetrasaccharide, GM3 trisaccharide, galactose β 1,3-N-acetylgalactosamine, lactose, and sialic acid and uses a solid substrate with functional groups liable to bind to the amine groups of the saccharides so that the saccharides are directly immobilized on the surface of the solid substrate.

In this manner, the present invention makes the use of the chemical modification and covalent bonding on the carbohydrates constituting ganglioside to directly immobilize the saccharides on the solid substrate without changing the structure or orientation of the saccharides, so it can detect the interaction between the saccharides and cholera toxin with ease and achieve simultaneous analysis with a small amount of sample.

Actually, the carbohydrate chip of the present invention can detect cholera toxin at the limit of detection (LOD) of 2 ng/mL (23 pM) as determined from the dose-response curve and 5 ng/mL (57.5 pM) as visually determined, provided that the limit of detection (LOD) of cholera toxin is defined as the limit of detection (LOD) of cholera toxin at which the fluorescence intensity is three times higher than the standard deviation of the fluorescent signal intensity when there is no cholera toxin sample (See FIG. 3).

Such a limit of detection (LOD) range supports the fact that the carbohydrate chip of the present invention is superior in detection sensitivity to the conventional monosaccharide-based microarray technique (Ngundi, M M, Taitt, C R, McMurry, S A, Kahne, D, Ligler, F S, 2006. Biosens. Bioelectron. 21: 1195-1201) or the disaccharide-based color transformation analysis (Schofield, C L, Field, R A, Russell, D A, 2007. Anal. Chem. 79: 1356-1361).

By using seven carbohydrates directly immobilized as capture probes, the carbohydrate chip of the present invention can detect cholera toxin more sensitively at a limit of detection (LOD) of 5 ng/mL (57.5 pM), predict the concentration of cholera toxin in the sample with different detection limits of the individual carbohydrate probes, and secure more precise results and determination due to the use of multiple probes.

According to a preferred embodiment, the present invention provides a carbohydrate chip for detection of *Vibrio cholera* that comprises a solid substrate; and GM1 pentasaccharide, GM2 tetrasaccharide, asialo GM1 tetrasaccharide, GM3 trisaccharide, galactose-β 1,3-N-acetylgalactosamine, lactose, and sialic acid immobilized on the surface of the solid substrate, where the visual limit of detection (LOD) of cholera toxin is 5 ng/mL.

Preferably, the carbohydrate chip of the present invention may comprise GM1 pentasaccharide in a concentration range of 250 to 500 μM.

Preferably, the carbohydrate chip of the present invention may use the solid substrate as selected from the group consisting of, if not specifically limited to, polymer, glass, gold, paper, and membrane.

Preferably, an amine group (—$NH_2$) may be introduced into the GM1 pentasaccharide, GM2 tetrasaccharide, asialo GM1 tetrasaccharide, GM3 trisaccharide, galactose-β 1,3-N-acetylgalactosamine, lactose, and sialic acid that are included in the carbohydrate chip of the present invention.

Preferably, at least one functional group selected from the group consisting of aldehyde, ketone, N-hydroxysuccinimide, epoxide, imidoester, anhydride, and carbonate may be introduced into the solid substrate that is included in the carbohydrate chip of the present invention.

Preferably, the carbohydrate chip of the present invention may be fabricated by:

introducing an amine group (—$NH_2$) into the GM1 pentasaccharide, GM2 tetrasaccharide, asialo GM1 tetrasaccharide, GM3 trisaccharide, galactose-β 1,3-N-acetylgalactosamine, lactose, and sialic acid;

introducing at least one functional group selected from the group consisting of aldehyde, ketone, N-hydroxysuccinimide, epoxide, imidoester, anhydride, and carbonate into the solid substrate; and immobilizing the GM1 pentasaccharide, GM2 tetrasaccharide, asialo GM1 tetrasaccharide, GM3 trisaccharide, galactose-β 1,3-N-acetylgalactosamine, lactose, and sialic acid on the solid substrate.

In accordance with another embodiment, the present invention is directed to a method for detecting *Vibrio cholera* that comprises:

(a) introducing an amine group (—NH$_2$) into the GM1 pentasaccharide, GM2 tetrasaccharide, asialo GM1 tetrasaccharide, GM3 trisaccharide, galactose-β 1,3-N-acetylgalactosamine, lactose, and sialic acid;

(b) introducing at least one functional group selected from the group consisting of aldehyde, ketone, N-hydroxysuccinimide, epoxide, imidoester, anhydride, and carbonate into the solid substrate; and (c) immobilizing the GM1 pentasaccharide, GM2 tetrasaccharide, asialo GM1 tetrasaccharide, GM3 trisaccharide, galactose-β 1,3-N-acetylgalactosamine, lactose, and sialic acid on the solid substrate.

In the step (a), a compound having an amine group, preferably aminoethyl aniline or aminobenzylamine, can be reacted with a saccharide in order to introduce an amine group into the saccharides. In this case, the aldehyde group contained in the saccharide receives electrons from the nitrogen atom of the amine group of the amine compound through the schiff base reaction to form a bond, —CH=N—. For this reaction, the amine compound can be dissolved in a solvent, which is easily selected depending on the type of the amine compound by those skilled in the art. For example, aminoethyl aniline can be dissolved in acetic acid, acetone, acetonitrile, etc. Preferably, one mole of the amine compound is reacted with one mole of the saccharide. If not specifically limited, the reaction time is preferably 30 minutes to 2 hours at 20 to 90° C., most preferably one hour at 40° C.

Further, the saccharide with the amine group may be reduced in order to immobilize the saccharide more firmly by stabilizing the bond (—CH=N—) formed by the reaction between the saccharide and the amine compound. Through the reduction process, the saccharide with the amine group can have a bond, —CH$_2$—NH—. If not specifically limited, the reducing agent used in the reduction process may be preferably at least one selected from the group consisting of dimethylamine borane, sodium borohydride, and cyanoborohydride. If not specifically limited, 1 to 10 moles of the reducing agent is preferably used for one mole of the saccharide with the amine group. If not specifically limited, the reducing agent may be preferably treated at 20 to 80° C. for one to two hours.

In the step (b), the solid substrate to be used as a substrate for the carbohydrate chip is treated to include a functional group liable to bind to the amine group of the saccharide. The functional group is, if not specifically limited to, aldehyde, ketone, N-hydroxysuccinimide, epoxide, imidoester, anhydride, or carbonate, preferably N-hydroxysuccinimide. A method known to those skilled in the art may be used to provide the solid substrate with a functional group; otherwise, a solid substrate with a functional group commercially available may be used. For example, a glass slide treated with N-hydroxysuccinimide is commercially available.

In the step (c), a coating technique known to those skilled in the art may be used in order to immobilize the amine-introduced saccharide. If not specifically limited, the saccharide may be immobilized on the surface of the solid substrate, preferably by spraying, jetting, painting, dipping, spotting, roll coating, or flow coating, most preferably by spotting the amine-introduced saccharide with a pin.

For a specific example, a solution containing the saccharide of the present invention may be spotted on the chip substrate treated with N-hydroxysuccinimide using a micropipette or a microarrayer. After completion of the spotting, the substrate is kept under humidity of about 75% for 12 hours or longer, washed out, and then dried with an inert gas such as argon (Ar) gas to complete a carbohydrate chip. Additionally, a defined washing process may be conducted in order to inactivate the unreacted N-hydroxysuccinimide on the completed carbohydrate chip.

In accordance with a still another embodiment, the present invention is directed to a method for detecting *Vibrio cholerae* that comprises: applying a sample containing cholera toxin onto the carbohydrate chip; and detecting the cholera toxin by fluorescence image analysis.

In this regard, the whole cholera toxin may be applied in order to detect cholera toxin secreted by *Vibrio cholerae* on the carbohydrate chip. As *Vibrio cholerae* secrets the whole cholera toxin other than cholera toxin B subunits, the carbohydrate chip of the present invention detects the whole cholera toxin to determine the existence of *Vibrio cholerae*.

Accordingly, the term "cholera toxin" as used herein preferably refers to the whole cholera toxin consisting of one A subunit and five B subunits.

Further, the term "sample containing cholera toxin" as used herein preferably means a bio-sample presumably containing *Vibrio cholerae*, such as water, food, blood, urine, or saliva.

The step of detecting cholera toxin by fluorescence image analysis may involve conducting a fluorescence image analysis on the antibody labeled with a fluorescent substance.

To determine whether or not the saccharide binds to cholera toxin, a primary antibody for detecting cholera toxin is applied to react with the cholera toxin bound to the saccharide, and a secondary antibody labeled with a fluorescent substance that is liable to bind to the primary antibody is then applied. The fluorescent substance is not specifically limited and may include Cy3 (green), Cy5 (red), FITC (green), Alexa, BODIPY, Rhodamine, or Q-dot. More than one of the secondary antibody reacts with different epitopes on the primary antibody, in which case the signal is amplified to facilitate visual determination of the interaction between the saccharide and the cholera toxin by way of the fluorescence image analysis method known to those skilled in the art.

Figure 3A:
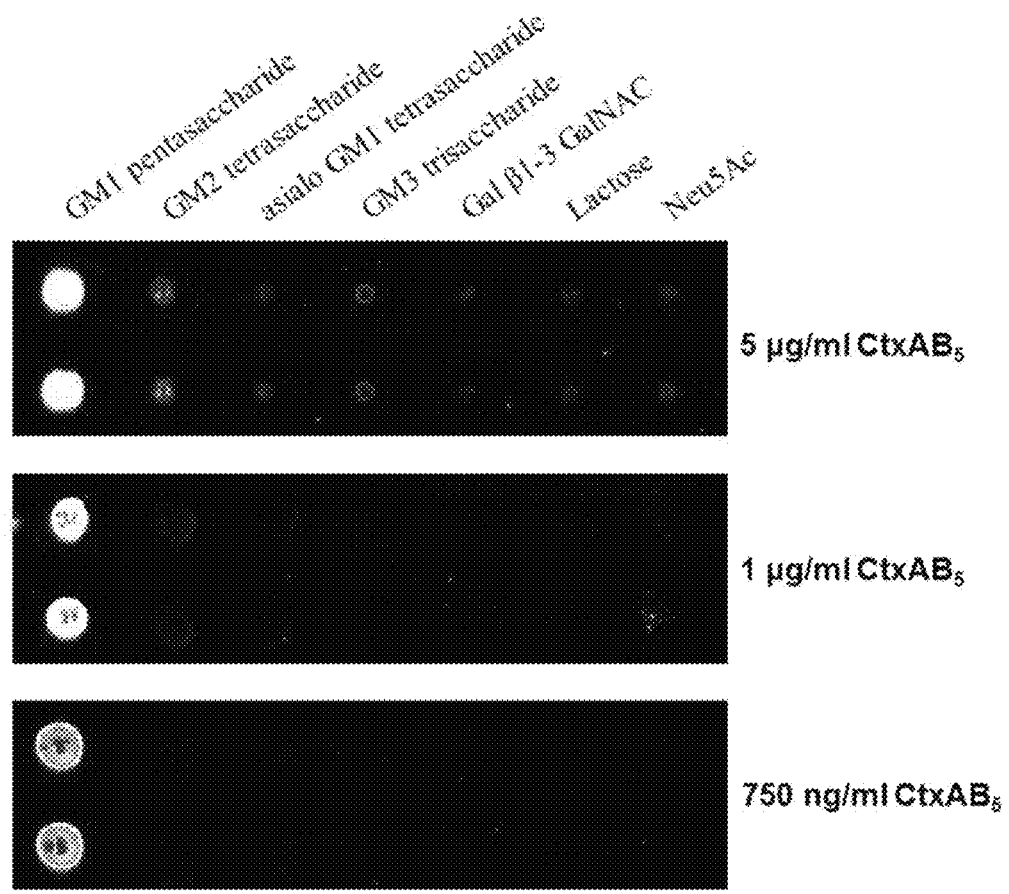
FIG. 3a is a fluorescence image analyzing the whole cholera toxin (ctxAB$_5$) of different concentrations (from 750 ng/ml to 5 μg/ml) as detected with the carbohydrate chip of the present invention consisting of seven carbohydrates (i.e., GM1 pentasaccharide, GM2 tetrasaccharide, asialo GM1 tetrasaccharide, GM3 trisaccharide, galactose-β 1,3-N-acetylgalactosamine, lactose, and sialic acid).
Figure 3C:
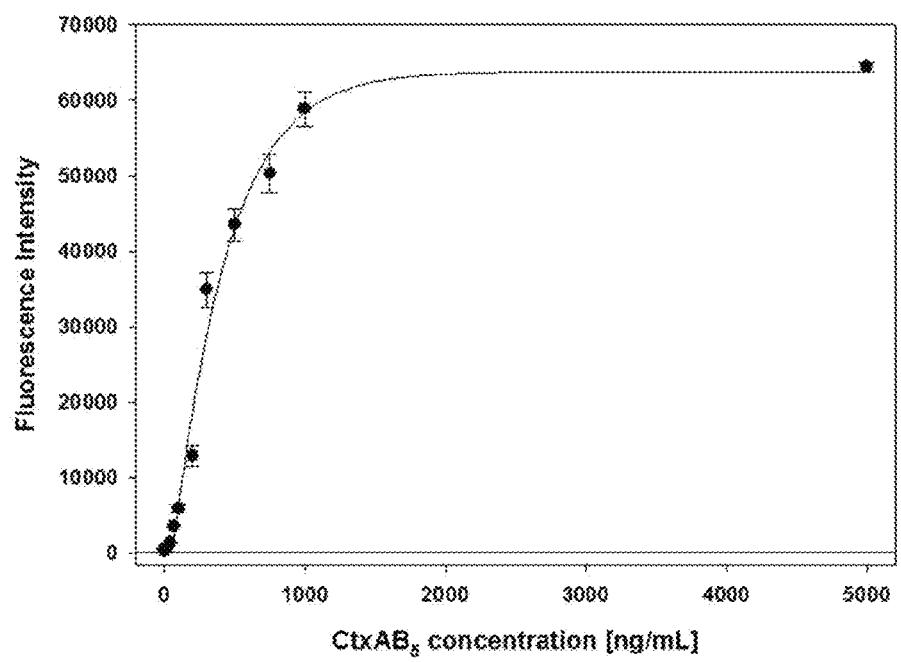
FIG. 3c is a line graph analyzing the fluorescence intensity shown in FIG. 3b.
Figure 3D:
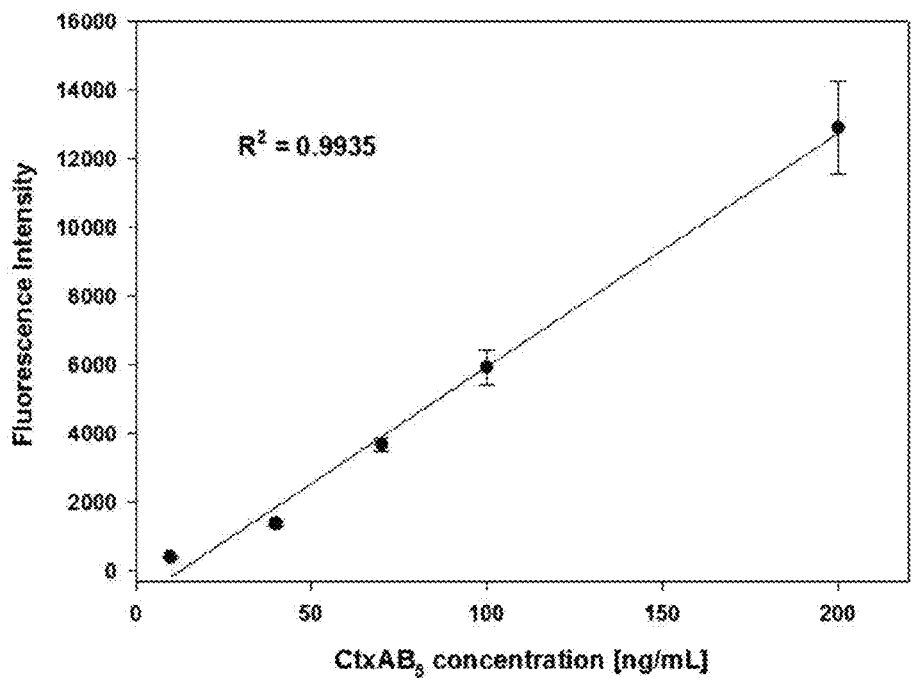
FIG. 3d is a line graph analyzing the partial interval of FIG. 3c.
Figure 4A:
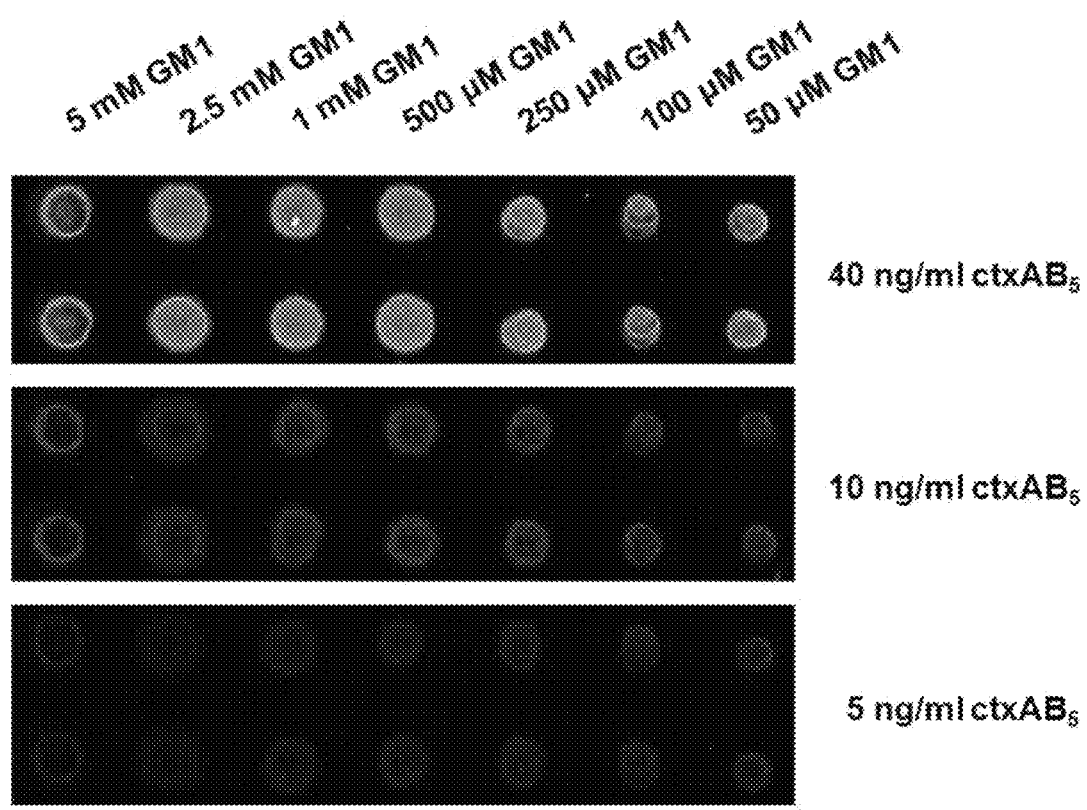
FIG. 4a is an entire fluorescence image analyzing the interaction between the whole cholera toxin (5, 10, or 40 ng/ml) and GM1 pentasaccharide (50, 100, 250, or 500 μg, 1, 2.5, or 5 mg) depending on the concentration on the carbohydrate chip of the present invention using the fluorescence immunoassay.
Figure 4B:
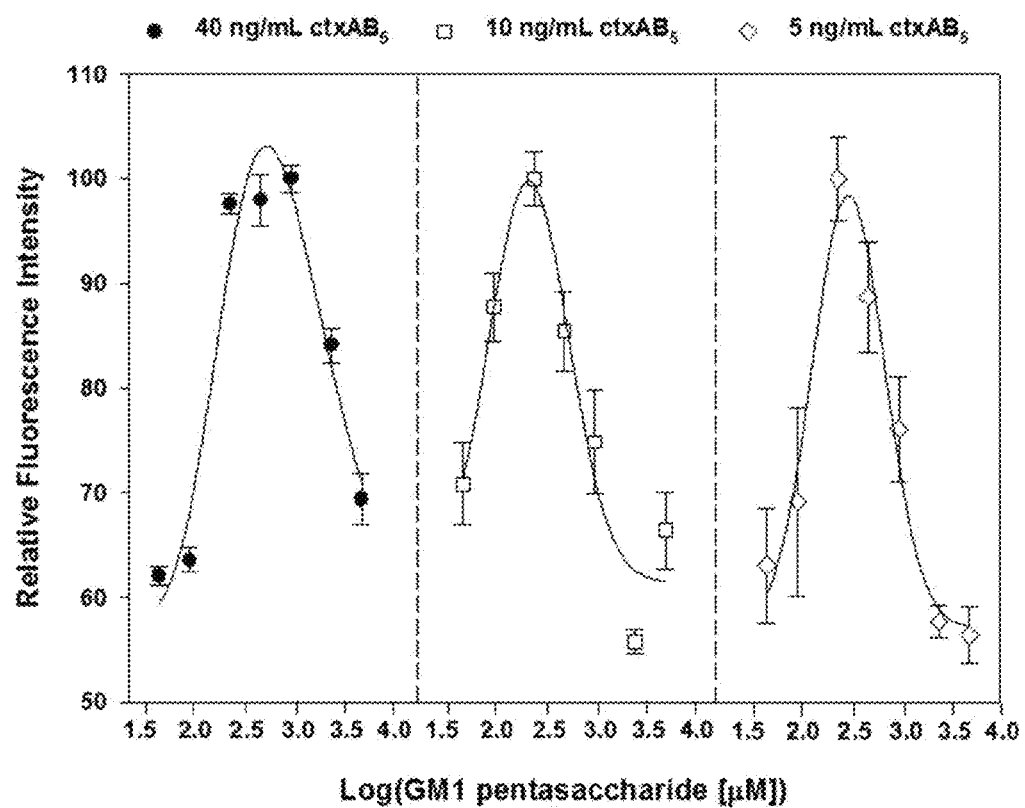

The present invention compares the intensity of fluorescence of GM1 pentasaccharide, GM2 tetrasaccharide, asialo GM1 tetrasaccharide, GM3 trisaccharide, galactose-β 1,3-N-acetylgalactosamine, lactose, and sialic acid on the carbohydrate chip, to detect the cholera toxin secreted by *Vibrio cholerae* and analyze the capture probe for detecting cholera toxin (See FIGS. 3, 4 and 5).

Accordingly, the carbohydrate chip of the present invention can be used to detect the cholera toxin secreted by *Vibrio cholerae* and further applied to the detection of *Vibrio cholerae* in food.

Hereinafter, the present invention will be described in detail with reference to the following examples, which are given only to exemplify the present invention and not intended to limit the scope of the present invention.

Example 1

Fabrication of Carbohydrate Chip 100 mM of saccharides (i.e., GM1 pentasaccharide, GM2 tetrasaccharide, asialo GM1 tetrasaccharide, GM3 trisaccharide, galactose-β 1,3-N-acetylgalactosamine, lactose, and sialic acid) dissolved in water and 100 mM of aminoethyl aniline dissolved in 100% acetic acid were mixed at a volume ratio of 1:1, and the aldehyde group of the saccharides was reacted with the amine group of the aniline at 40° C. for one hour to introduce an amine group into the saccharides through the schiff base reaction. After completion of the reaction, 100 mM of dimethylamine borane was added to cause a reduction reaction for about one hour.

The amine-introduced saccharides were dissolved in a print buffer (at pH 8.5) consisting of 150 mM of phosphate, 0.04% Tween-20, 5% glycerol, and 0.1 mg/ml of bovine serum albumin (BSA) and then spotted on a glass slide (Schott Nexterion, Germany) treated with N-hydroxysuccinimide at humidity of 75% using a pin (Chip Maker 2) and a microarrayer (Microssys 5100). The glass slide was kept under the same humidity condition for 12 hours or longer to immobilize the saccharides to complete a carbohydrate chip. FIG. 1 shows a flat form of the carbohydrate chip.

Example 2

Detection of Cholera Toxin Using Carbohydrate Chip

To inactivate the unreacted N-hydroxysuccinimide on the carbohydrate chip prepared in Example 1, a blocking solution (pH 8.0) containing 5 mM of ethanol amine dissolved in 50 mM of sodium borate was added for one-hour reaction. After completion of the reaction, the blocking solution was removed, and the remainder of the blocking solution was washed away with a washing buffer I consisting of 137 mM of NaCl, 2.7 mM of potassium chloride, 4.3 mM of disodium hydrogen phosphate ($Na_2HPO_4$), 1.4 mM of potassium dihydrogen phosphate ($KH_2PO_4$), and 0.5% Tween-20 and a washing buffer II (pH 7.5) having the same composition of the washing buffer I except for 0.5% Tween-20. Then, a centrifugal machine was used for drying.

The cholera toxin is known to form a strong bond specific to the saccharide moiety of GM1 ganglioside. But, the present invention used GM2 tetrasaccharide, asialo GM1 tetrasaccharide, GM3 trisaccharide, galactose-β 1,3-N-acetylgalactosamine, lactose, and N-acetylneuraminic acid, as well as GM1 pentasaccharide, as capture probes for detection of cholera toxin. Further, the cholera toxin used to determine whether the cholera toxin is detectable with the carbohydrate chip of the present invention is the whole cholera toxin other than the cholera toxin B subunit. This is because *Vibrio cholerae* secrets the whole cholera toxin rather than the cholera toxin B subunit.

For quantitative analysis, the whole cholera toxin of different concentrations (0 to 10 μg/ml) was applied onto the carbohydrate chip of the present invention and detected by the fluorescence immune method using an antibody to the cholera toxin B subunit produced by a rabbit and a secondary antibody bound to a fluorescent dye (Alexa Fluor 546).

2-1. Determination of Limit Of Detection (LOD) for Cholera Toxin

To determine the sensitivity and the limit of detection (LOD) of the carbohydrate chip of the present invention, 10 mM of seven carbohydrates (i.e., GM1 pentasaccharide, GM2 tetrasaccharide, asialo GM1 tetrasaccharide, GM3 trisaccharide, galactose-β 1,3-N-acetylgalactosamine, lactose, and sialic acid) was used as capture probes. The sensitivity and the limit of detection (LOD) were determined from the dose-response curve. The limit of detection (LOD) refers to the lowest concentration at which the fluorescence intensity is three times higher than the standard deviation of the fluorescence intensity when there is no sample.

According to the definition, as can be seen from FIGS. 3b, 3c and 3d, the carbohydrate chip of the present invention had a LOD of 2 ng/mL (23 pM), but with a visual LOD of 5 ng/mL (57.5 pM), when GM1 pentasaccharide was used as a capture probe. Such a limit of detection (LOD) demonstrated that the carbohydrate chip of the present invention was superior in detection sensitivity to the conventional saccharide-based microarray (Ngundi, M M, Taitt, C R, McMurry, S A, Kahne, D, Ligler, F S, 2006. Biosens. Bioelectron. 21: 1195-1201) or the disaccharide-based color transformation analysis (Schofield, C L, Field, R A, Russell, D A, 2007. Anal. Chem. 79: 1356-1361). Further, the fluorescence intensity in the concentration range of the whole cholera toxin from 1 μg/mL to 5 ng/mL increased with an increase in the concentration of the whole cholera toxin. It was observed that the fluorescence intensity in the concentration range of the whole cholera toxin from 10 ng/mL to 200 ng/mL and the concentration of the whole cholera toxin had a linear relation having a high coefficient of determination of 0.9935. The fluorescence intensity was saturated when the concentration of the whole cholera toxin was 1 μg/mL or greater.

As shown in FIG. 3a, the visual limit of detection (LOD) was 750 ng/mL when using GM2 tetrasaccharide as a capture probe. The visual limit of detection (LOD) was 1 μg/mL when using asialo GM1 tetrasaccharide as a capture probe. The carbohydrate chip was proved to detect cholera toxin at 5 μg/mL or above when using the other carbohydrates, i.e., GM3 trisaccharide, galactose-β 1,3-N-acetylgalactosamine, lactose, and sialic acid.

Using seven carbohydrates as capture probes, the carbohydrate chip of the present invention was able to detect cholera toxin at a visual limit of detection (LOD) of 5 ng/mL (57.5 pM) more sensitively, predict the concentration of cholera toxin in the sample with different detection limits of the individual carbohydrate probes, and secure more precise results and determination due to the use of multiple probes.

2-2. Determination of Optimum Concentration of Saccharide for Detection of Cholera Toxin The ligand density is known to be a very important factor in the polyvalent bonding system, since it determines the distribution of ligands and the distance between ligands (Mammen, M, Choi, S K, Whitesides, G M, 1998. Angew. Chem. Int. Ed. 37: 2754-2794; Kiessling, L L, Gestwicki, J E, Strong, L E, 2006. Angew. Chem. Int. Ed. 45: 2348-2368; Smith, E A, Thomas, W D, Kiessling L L, Corn, R M, 2003. J. Am. Chem. Soc. 125: 6140-6148; Huskens, J, Mulder, A, Auletta, T, Nijhuis, C A, Ludden, M J W, Reinhoudt, D N J, 2004. J. Am. Chem. Soc. 126: 6784-6797). Shi et al. disclosed that the strength of bond decreased with an increase in the density of GM1 according to GM1 clustering (Shi J, Yang, T, Kataoka, S, Zhang, Y, Daiz, A J, Cremer, P S, 2007. GM1 Clustering Inhibits Cholera Toxin Binding in Supported Phospholipid Membranes. J. Am. Chem. Soc. 129: 5954-5961). Another research groups analyzed the binding degree of cholera toxin to the intestinal microvillar membrane having different GM1 densities and reported that the cholera toxin had a stronger binding degree with a decrease in the concentration of GM1 (Lencer, W I; Chu, S H; Walker, W A, 1987. Differential Binding Kinetics of Cholera Toxin to Intestinal Microvillus Membrane during Development. Infect. Immunol. 55: 3126-3130). The results of these studies imply that the density of GM1 pentasaccharide had an effect on the detection of cholera toxin using the carbohydrate chip and was a major determinant of the sensitivity of the carbohydrate chip according to the present invention.

To analyze the effect of the concentration of GM1 pentasaccharide on determination of cholera toxin, 50 μM to 5 mM of GM1 pentasaccharide and 5 to 40 ng/mL of the whole cholera toxin were used. As shown in FIG. 4, the fluorescence intensity increased with a decrease in the concentration of GM1 pentasaccharide ranging from 250 μM to 1 mM, and the optimum concentration of GM1 pentasaccharide for detection of cholera toxin was in the range of 250 to 500 μM. Accordingly, the carbohydrate chip of the present invention had an optimum concentration of GM1 pentasaccharide for detection of cholera toxin (ranging from 250 to 500 μM), and its sensitivity was enhanced by adopting the optimum concentration of GM1 pentasaccharide.

Example 3

Detection of Cholera Toxin Secreted from *Vibrio Cholerae* Culture Using Carbohydrate Chip There has been a demand for fast and high-sensitivity analyses for *Vibrio cholerae*, since many people suffer from water or foods contaminated with *Vibrio cholerae*. For that reason, an experiment was carried out to determine whether the carbohydrate chip of the present invention was capable of detecting cholera toxin from the actual *Vibrio cholerae* culture. The experiment used the carbohydrate chip consisting of seven carbohydrates (i.e., GM1 pentasaccharide, GM2 tetrasaccharide, asialo GM1 tetrasaccharide, GM3 trisaccharide, galactose-β 1,3-N-acetylgalactosamine, lactose, and sialic acid) as prepared in Example 1. The conditions of the experiment were the same as defined in the quantitative analysis using the whole cholera toxin. To determine whether the carbohydrate chip was enabled to overcome the long culture time required in detecting dangerous microorganism *Vibrio cholerae*, the experiment was conducted after culturing *Vibrio cholerae* in an AKI culture medium at 37° C. for 3 hours. Without additional treatments, the *Vibrio cholerae* culture was applied onto the carbohydrate chip of the present invention. As controls, *Vibrio parahaemolyticus* and *Staphylococcus aureus* were cultured in an LB culture medium at 37° C. for 12 hours and then applied onto the carbohydrate chip of the present invention.

Figure 5A:
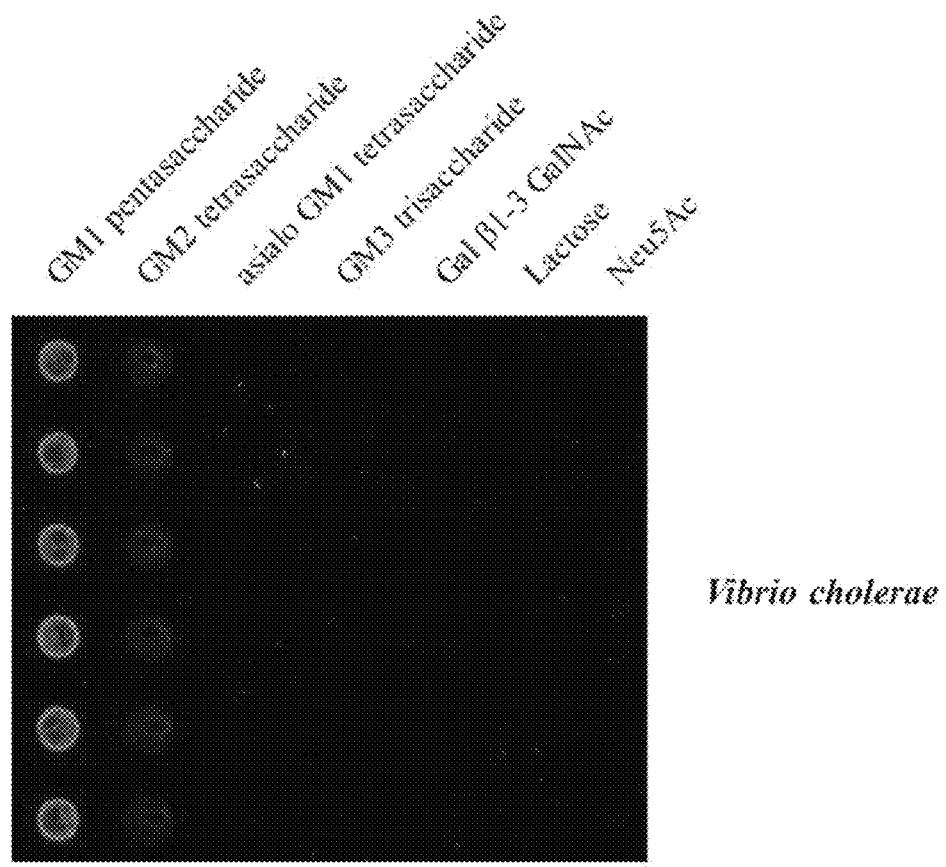
FIG. 5a is an entire fluorescence image analyzing the detection of cholera toxin using the fluorescence immunoassay, where a *Vibrio cholerae* culture is applied on the carbohydrate chip of the present invention.
Figure 5B:
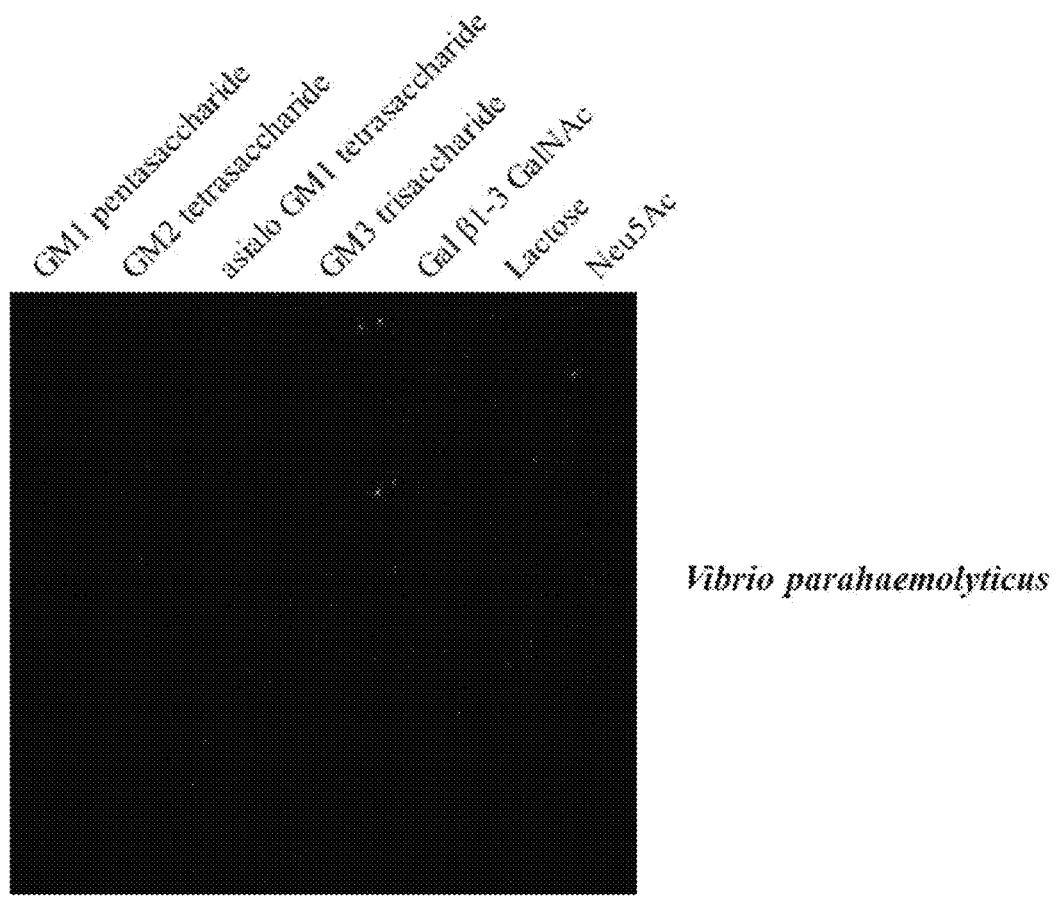
FIG. 5b is an entire fluorescence image analyzing the detection of cholera toxin using the fluorescence immunoassay, where a *Vibrio parahaemolyticus* culture is applied on the carbohydrate chip of the present invention.
Figure 5C:
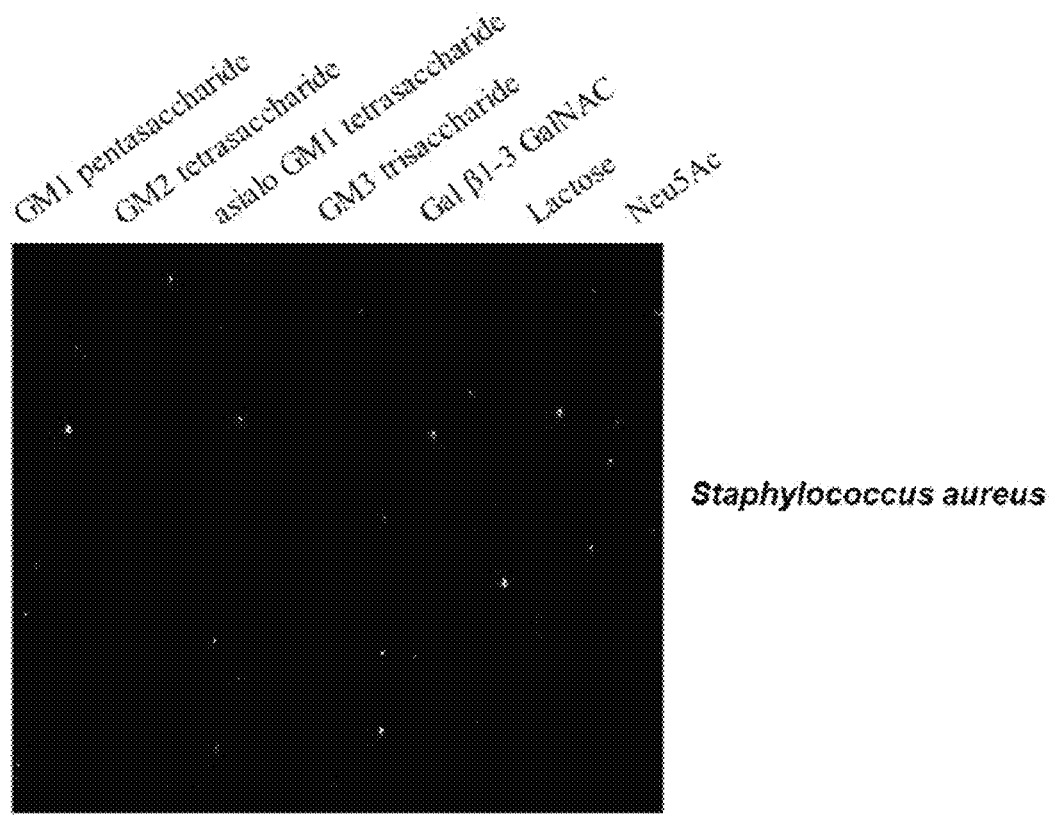
FIG. 5c is an entire fluorescence image analyzing the detection of cholera toxin using the fluorescence immunoassay, where a *Staphylococcus aureus* culture is applied on the carbohydrate chip of the present invention.
Figure 5D:
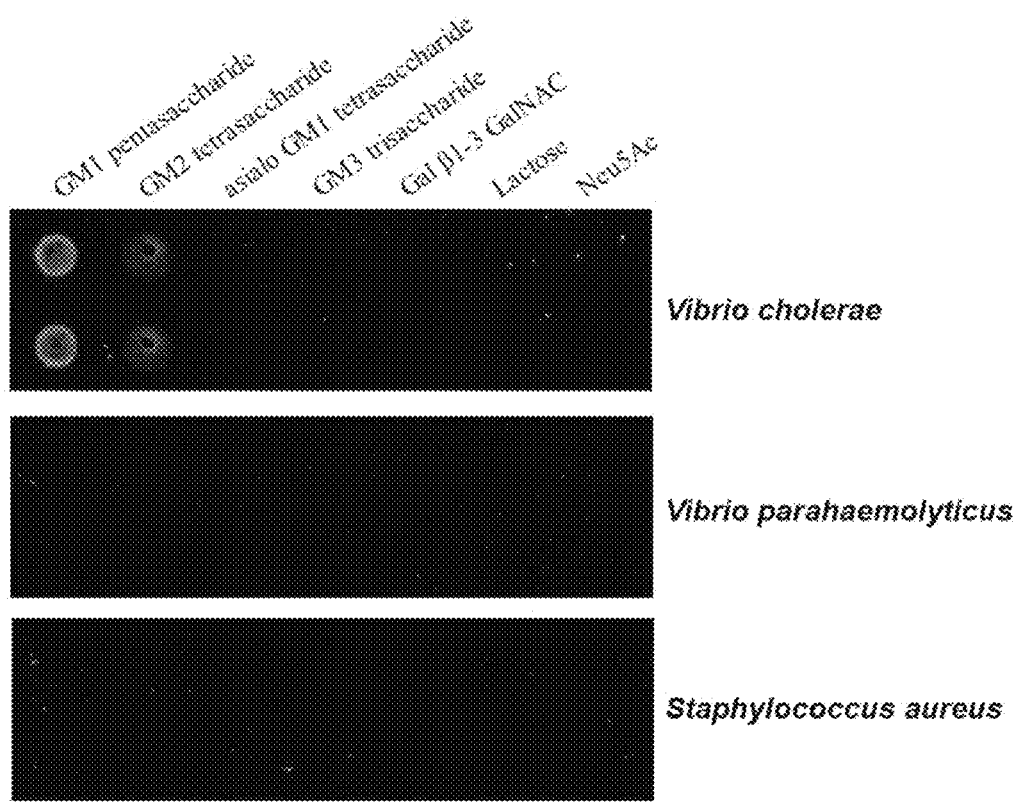
FIG. 5d is a diagram summing up the fluorescence images of FIGS. 5a, 5b and 5c.

As a result, as shown in FIG. 5a, the carbohydrate chip of the present invention had high fluorescence intensity for GM1 pentasaccharide and GM2 tetrasaccharide and detected cholera toxin, thereby demonstrating the detectability of *Vibrio cholerae*. It can be seen from the aforementioned analysis results on the limit of detection (LOD) of the whole cholera toxin that the fluorescence signal was observed only from GM1 pentasaccharide and GM2 tetrasaccharide, implying that there exists cholera toxin at concentration of 5 g/ml or below. Further, a *Vibrio parahaemolyticus* culture and a *Staphylococcus aureus* culture as controls were applied onto the carbohydrate chip of the present invention in order to evaluate the specificity of the carbohydrate chip of the present invention. As a result, as shown in FIGS. 5b and 5c, the carbohydrate chip of the present invention had no fluorescence signal from either the *Vibrio parahaemolyticus* culture or the *Staphylococcus aureus* culture but detected the fluorescence intensity for the cholera toxin produced only from the *Vibrio cholerae* culture. This revealed that the carbohydrate chip of the present invention had high specificity to the detection of cholera toxin.

Effect of the Invention

The present invention uses a carbohydrate chip immobilizing GM1 pentasaccharide, GM2 tetrasaccharide, asialo GM1 tetrasaccharide, GM3 trisaccharide, galactose-β 1,3-N-acetylgalactosamine, lactose, and sialic acid to detect cholera toxin secreted by *Vibrio cholerae* in a low concentration range. Such a chip-based method can detect cholera toxin simultaneously with a small amount of sample, thereby easily determining the existence of *Vibrio cholerae* in the sample.

What is claimed is:

1. A method for detecting *Vibrio cholerae* by detecting cholera toxin consisting of one A subunit and five B subunits, the method comprising:
   applying a sample containing cholera toxin onto a carbohydrate chip,
   wherein the carbohydrate chip comprises (i) a solid substrate and (ii) GM1 pentasaccharide, GM2 tetrasaccharide, asialo GM1 tetrasaccharide, GM3 trisaccharide, galactose-β 1,3-N-acetylgalactosamine, lactose, and sialic acid immobilized on a surface of the solid substrate,
   wherein the carbohydrate chip has a visual limit of detection (LOD) of 5 ng/mL for cholera toxin produced by *Vibrio cholera*; and
   detecting the cholera toxin by fluorescence image analysis.

2. The method according to claim 1, wherein the sample containing cholera toxin is a water sample, a food sample, a blood sample, a urine sample, or a saliva sample.

3. The method according to claim 1, wherein the solid substrate is selected from the group consisting of polymer, glass, gold, paper, and membrane.

4. The method according to claim 1, wherein an amine group ($-NH_2$) is introduced into the GM1 pentasaccharide, GM2 tetrasaccharide, asialo GM1 tetrasaccharide, GM3 trisaccharide, galactose-β1,3-N-acetylgalactosamine, lactose, and sialic acid.

5. The method according to claim 1, wherein at least one functional group selected from the group consisting of aldehyde, ketone, N-hydroxysuccinimide, epoxide, imidoester, anhydride, and carbonate is introduced into the solid substrate.

6. The method according to claim 1, wherein the carbohydrate chip is prepared by:
   introducing an amine group ($-NH_2$) into the GM1 pentasaccharide, GM2 tetrasaccharide, asialo GM1 tetrasaccharide, GM3 trisaccharide, galactose-β 1,3-N-acetylgalactosamine, lactose, and sialic acid;
   introducing at least one functional group selected from the group consisting of aldehyde, ketone, N-hydroxysuccinimide, epoxide, imidoester, anhydride, and carbonate into the solid substrate; and
   immobilizing the GM1 pentasaccharide, GM2 tetrasaccharide, asialo GM1 tetrasaccharide, GM3 trisaccharide, galactose-β 1,3-N-acetylgalactosamine, lactose, and sialic acid on the solid substrate.

* * * * *